(12) United States Patent
Stark (10) Patent No.: US 10,457,811 B2
(45) Date of Patent: Oct. 29, 2019

(54) SURFACE-MODIFIED CALCIUM OXIDE

(71) Applicant: Kalkfabrik Netstal AG, Netstal (CH)

(72) Inventor: Wendelin Jan Stark, Langenthal (CH)

(73) Assignee: Kalkfabrik Netstal AG, Nestal (CH)

( * ) Notice: Subject to any disclaimer, the term of this patent is extended or adjusted under 35 U.S.C. 154(b) by 0 days.

(21) Appl. No.: 15/437,889

(22) Filed: Feb. 21, 2017

(65) Prior Publication Data

US 2017/0158860 A1 Jun. 8, 2017

Related U.S. Application Data

(62) Division of application No. 14/442,751, filed as application No. PCT/CH2013/000180 on Oct. 18, 2013, now Pat. No. 9,611,175.

(30) Foreign Application Priority Data

Nov. 15, 2012 (EP) ..................................... 12007737

(51) Int. Cl.

| | | |
|---|---|---|
| *C09C 1/00* | (2006.01) | |
| *C09C 1/02* | (2006.01) | |
| *A01N 25/26* | (2006.01) | |
| *A61K 8/02* | (2006.01) | |
| *A61K 9/14* | (2006.01) | |
| *C08K 9/00* | (2006.01) | |
| *C09J 11/04* | (2006.01) | |
| *D21H 17/67* | (2006.01) | |
| *C09D 7/62* | (2018.01) | |
| *C04B 22/06* | (2006.01) | |
| *C01F 11/02* | (2006.01) | |
| *A23L 33/10* | (2016.01) | |
| *A61K 8/36* | (2006.01) | |
| *A61Q 11/00* | (2006.01) | |
| *A61Q 19/00* | (2006.01) | |
| *A61K 8/85* | (2006.01) | |
| *A61K 8/19* | (2006.01) | |
| *C09D 7/40* | (2018.01) | |
| *A01N 59/00* | (2006.01) | |
| *A61K 47/02* | (2006.01) | |
| *C08K 3/22* | (2006.01) | |
| *C08K 9/04* | (2006.01) | |
| *C09D 201/00* | (2006.01) | |
| *C09J 201/00* | (2006.01) | |
| *D21H 19/38* | (2006.01) | |
| *C09C 3/00* | (2006.01) | |
| *C09C 3/04* | (2006.01) | |
| *C09C 3/08* | (2006.01) | |

(52) U.S. Cl.
CPC ................ *C09C 1/02* (2013.01); *A01N 25/26* (2013.01); *A01N 59/00* (2013.01); *A23L 33/10* (2016.08); *A61K 8/0241* (2013.01); *A61K 8/19* (2013.01); *A61K 8/361* (2013.01); *A61K 8/85* (2013.01); *A61K 9/141* (2013.01); *A61K 47/02* (2013.01); *A61Q 11/00* (2013.01); *A61Q 19/00* (2013.01); *C01F 11/02* (2013.01); *C04B 22/064* (2013.01); *C08K 3/22* (2013.01); *C08K 9/00* (2013.01); *C08K 9/04* (2013.01); *C09D 7/62* (2018.01); *C09D 7/68* (2018.01); *C09D 7/69* (2018.01); *C09D 201/00* (2013.01); *C09J 11/04* (2013.01); *C09J 201/00* (2013.01); *D21H 17/675* (2013.01); *D21H 19/385* (2013.01); *A23V 2002/00* (2013.01); *A61K 2800/10* (2013.01); *A61K 2800/412* (2013.01); *C01P 2004/51* (2013.01); *C01P 2004/61* (2013.01); *C01P 2004/62* (2013.01); *C01P 2006/80* (2013.01); *C08K 2003/2206* (2013.01); *C09C 3/006* (2013.01); *C09C 3/041* (2013.01); *C09C 3/08* (2013.01); *Y02P 20/582* (2015.11)

(58) Field of Classification Search
CPC ...... A01N 25/26; A61K 8/0241; A61K 9/141; D21H 17/675; C04B 22/064; C04B 20/1022; C04B 20/026; B01J 20/3085; B01J 20/2803; B01J 20/06; B01J 20/22; B01J 20/041; B01J 20/223; C09D 7/1225; C09C 1/02; C08K 9/00; C09J 11/04; C01G 45/02; C01G 9/02
USPC ........... 423/635, 636, 274; 516/33; 428/403; 424/490, 401, 417; 426/654; 427/215; 523/200; 106/461, 471; 162/181.4; 252/181.4, 181.7, 194; 502/401
See application file for complete search history.

(56) References Cited

U.S. PATENT DOCUMENTS 3,138,563 A 6/1964 Morgan et al.
3,951,849 A * 4/1976 Vickery ............... B01J 13/0086
106/429

(Continued)

FOREIGN PATENT DOCUMENTS

CH 640 201 A5 12/1978
DE 102006015774 10/2007

(Continued)

OTHER PUBLICATIONS

International Search Report for corresponding International Application No. PCT/CH2013/000180 dated Feb. 3, 2014.

(Continued)

*Primary Examiner* — Steven J Bos
(74) *Attorney, Agent, or Firm* — Renner, Otto, Boisselle & Sklar, LLP (57) ABSTRACT

The present invention relates to methods for producing surface-modified calcium oxide particles having the production steps according to claim 1, novel calcium oxide particles obtained according to these methods, and uses thereof.

13 Claims, 1 Drawing Sheet

(56) References Cited

U.S. PATENT DOCUMENTS

| | | | |
|---|---|---|---|
| 4,208,388 A | 6/1980 | Nicholson | |
| 7,754,642 B2 * | 7/2010 | Katay | C02F 1/281 502/150 |
| 9,611,175 B2 * | 4/2017 | Stark | C04B 22/064 |
| 2002/0004099 A1 | 1/2002 | Ando | |
| 2009/0004098 A1 * | 1/2009 | Schmidt | B82Y 30/00 423/608 |
| 2009/0246524 A1 | 10/2009 | Ohmi et al. | |
| 2011/0182995 A1 | 7/2011 | Asgary | |
| 2013/0280335 A1 | 10/2013 | Han et al. | |

FOREIGN PATENT DOCUMENTS

| | | |
|---|---|---|
| EP | 0340313 | 11/1989 |
| WO | 1994/003536 A1 | 2/1994 |
| WO | 1995/015293 A1 | 6/1995 |
| WO | 2005/100246 A1 | 10/2005 |
| WO | 2007038128 | 4/2007 |
| WO | 2007/092006 A1 | 8/2007 |
| WO | 2013182917 A1 | 12/2013 |

OTHER PUBLICATIONS

Oates, Tony, "Lime and Limestone," Ullmann's Encyclopedia of Industrial Chemistry 5th Edition on CD-ROM, Wiley,1997.
Lexikon der Chemie "Calciumoxid, Ungelöschter Kalk, Gebrannter Kalk, Ätzkalk, E529, Branntkalk, " www.lebensmittellexikon.de/c0002530. (English translation: Calcium Oxide, Unlashed Lime, Burnt Lime, Quick-lime, E 529, quicklime.

* cited by examiner

SURFACE-MODIFIED CALCIUM OXIDE

This application is a divisional of U.S. application Ser. No. 14/442,751 filed May 14, 2015, which is a national phase of International Application No. PCT/CH2013/000180 filed Oct. 18, 2013, which claims priority to Application No. EP 12007737.5 filed Nov. 15, 2012.

The present invention relates to methods for producing surface-modified calcium oxide particles, novel calcium oxide particles obtained according to these methods, and uses thereof.

Limestone, burnt and hydrated lime are known technical products; details can be found in Kirk-Othmer (*Encyclopedia of Chemical Technology,* 2010, Wiley, keyword "lime and limestone"). Limestone is contained in numerous consumer goods, is used in industrial processes, and functions as a starting material for burnt lime (a mixture containing primarily calcium oxide) and hydrated lime (a mixture containing primarily calcium hydroxide). Burnt lime, in turn, is used as a starting material for hydrated lime. Calcium oxide is highly reactive and sensitive to water and moisture and, given the all-pervasive atmospheric moisture, has only found limited fields of application. The sensitivity to atmospheric moisture increases, the smaller the calcium oxide particles are, since the surface-to-mass ratio shifts in an unfavorable manner.

Nicholson (CH640201) and Brelowski et al (WO2007/092006) describe methods for producing burnt lime having improved flowability. According to this, milled burnt lime is mixed with specific siloxanes in a common commercial mixer. The thusly obtained calcium oxide particles have improved flow behavior. These materials are advantageous for specific applications in the metal industry; the particles are entirely unsuitable for numerous other applications, however, due to the siloxane modification thereof.

Nakamura et al (WO2005/100246) have recognized that the production of finely divided calcium oxide creates problems (page 2, last paragraph): "Accordingly, it has been impossible to produce high concentration slurry of calcium oxide nanoparticles by conventional techniques." and therefore propose a synthetic method proceeding from calcium diketonates. It is obvious that such a production method uses a great deal of energy, is expensive, and results in the formation of secondary products.

Chai et al (WO95/15293) likewise disclose a synthetic method for producing calcium oxide particles by means of decomposition of calcium carbonate in plasma. It is obvious that such a production method uses a great deal of energy and is expensive.

Bezze (WO94/03536) discloses a method for the production of anhydrous calcium oxide, which is coated with specific titanates or zirconates; furthermore, the use thereof as an additive in polymers is described. It is obvious that the starting materials that are used are highly specific and, due to the high price thereof, are unsuitable for general use. Furthermore, the use of these transition metals is considered to be disadvantageous in some applications due to the poor biological degradability.

One object of the present invention, therefore, is to provide an improved method for producing particulate calcium oxide having a modified surface. It is particularly significant to provide a method that operates cost-effectively and a corresponding system, which produces high-quality products. Furthermore, it is advantageous to minimize the amount of energy used and to use naturally occurring starting materials. Another object of the present invention is to provide modified calcium oxide particles and new fields of application for these materials.

The above-described problems are solved according to the independent claims. The dependent claims are advantageous embodiments.

The invention is described in detail in the following. The following terms have the meaning indicated herein, provided no other meaning results from the direct context.

The general, preferred, and particularly preferred embodiments, ranges, etc., mentioned in association with the present invention can be combined with one another in any manner. Likewise, individual definitions, embodiments, etc., can be omitted or may be irrelevant. The term "comprising" is intended to include the meanings "containing" and "consisting of".

Unless noted otherwise, percentages are indicated as % by mass.

The term "burnt lime" is known and, for example, is described in Kirk-Othmer (see above) and substantially contains CaO, typically >90% by mass. Therefore, burnt lime and calcium oxide will be used synonymously in the present invention. According to the present invention, calcium oxide is present as particulate material. In the context of the present invention, therefore, nanoparticles are defined as having a size range of 10 to 100 nm; correspondingly, submicron particles are defined as having a size range of 100 nm to 1000 nm, microparticles are defined as having a size range of 1 to 40 micrometers, preferably having a diameter of 1 to 10 micrometers. Particle sizes and distribution can be determined using known methods. Small particles (less than 10 micrometers in diameter) are measured, in particular, by means of optical detection (light scattering), microscopy (light microscopy or electron microscopy; measuring the individual particles and calculating the mean particle size), or in optical centrifuges (e.g., Lumisizer, LUM GmbH or in an X-ray disk centrifuge, for example, BI-XDC from "Brookhaven Instruments Corporation"), which directly deliver a hydrodynamic diameter.

The term "particle size" or "grain size" is used synonymously, is generally known, and can be determined using common methods. The particle size is given as the "mean particle size", provided nothing else arises in the present invention. For particles in the micrometer range (diameter greater than 10 micrometers), the measurement is preferably carried out by means of laser granulometry (for example, Sympatec HELOS). Screen analysis is preferably used for particles that are greater than 100 micrometers in size. A measure of 0-200 µm as the result of a screen analysis is intended to mean that the upper limit value for the particle size is 200 µm (for example, by determination of the screen residue by means of air-jet screening), but the lower limit value is in a meaningful technical range (for example, as given by a milling process).

The invention, and in particular the methods and materials, are described in greater detail in the following with reference to the figures. The letter (M) stands for mill/milling device, (S) stands for spraying device, (T) stands for separating device, (W) stands for heat exchanger, and r-CaO and m-CaO stand for raw and modified burnt lime, respectively, MH stands for milling aid, and Add stands for additive.

Figure 1:
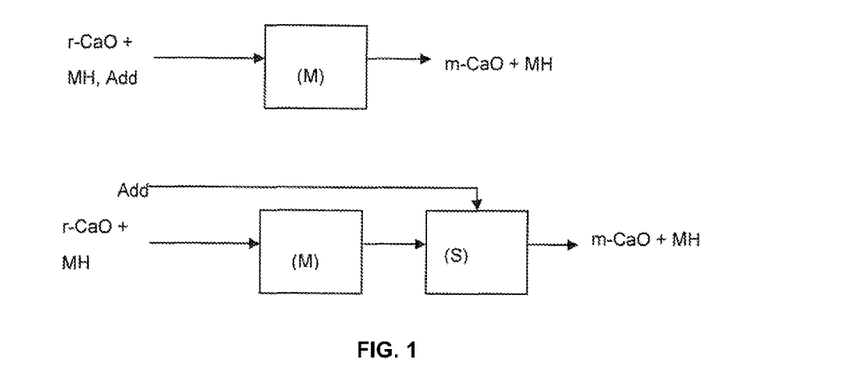
FIG. 1 shows, schematically, the method according to the invention for producing burnt lime, wherein the upper graphic shows the embodiment according to method (I) with simultaneous milling and modification by means of additives, and the lower graphic shows the embodiment according to method (II) with sequential steps for milling and modification by means of additives.
Figure 2:
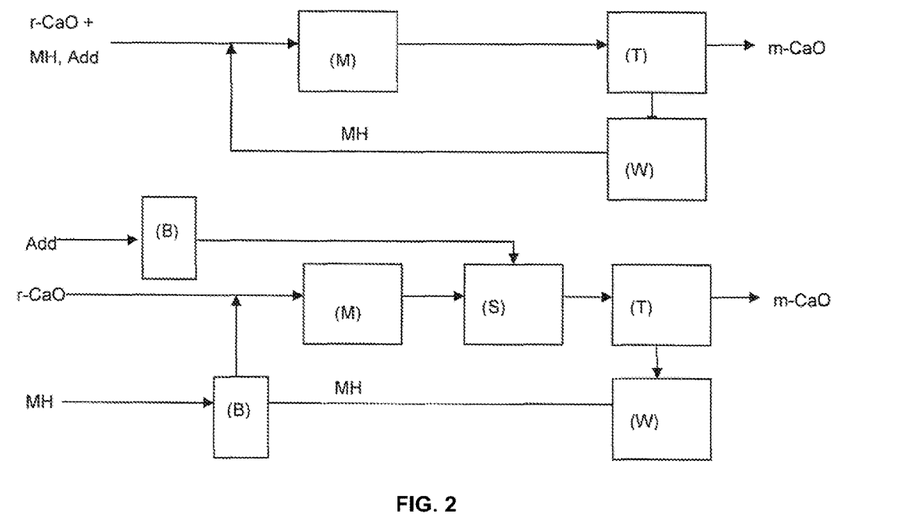
FIG. 2 shows, schematically, the method according to the invention for producing burnt lime with an additional separating and recycling step for the milling aid MH. Therein, the initially obtained mixture of modified burnt lime m-CaO and milling aid MH is separated in a separating device (T), the milling aid is cooled in a heat exchanger and is recycled into the process. The embodiment according to method (I) is depicted in the upper graphic and the embodiment according to method (II) is depicted in the lower graphic. In addition, the lower graphic shows the use of intermediate storage (B) for the additive and the milling aid.

In a first aspect, the invention therefore relates to a method for producing surface-modified calcium oxide particles from raw calcium oxide, additive(s), and milling aid(s) in an inert milling device that is sealed with respect to the surroundings.

In a first embodiment (method I), the invention relates to a method for producing surface-modified calcium oxide particles, comprising the steps of: (a) providing raw calcium oxide, additive, and milling aid; (b) providing and inertizing a milling aid (M) that has been sealed with respect to the surroundings; and (c) milling the raw calcium oxide in the presence of the milling aid and the additive in this milling device.

In a second embodiment (method II), the invention relates to a method for producing surface-modified calcium oxide particles, comprising the steps of: (a) providing raw calcium oxide, additive, milling aid; (b) providing and inertizing a milling aid (M) and a spraying device (S) that have been sealed with respect to the surroundings; (c) milling the raw calcium oxide in the presence of the milling aid in the aforementioned milling device (M); and (d) contacting the milled calcium oxide with the additive in the aforementioned spraying device (S).

The methods (I) and (II) therefore differ substantially according to whether the milling of the raw calcium oxide and the contacting with additive take place simultaneously (method I) or in sequential steps (method II). In both methods, further steps can be added at the beginning and/or downstream. This aspect of the invention, including a description of the individual process steps and the apparatuses and starting materials used, will be explained in the following.

Starting materials: The starting materials, raw calcium oxide (r-CaO), additive(s) (Add), milling aid (MH) are known per se and are commercially available or can be produced according to generally known methods. According to the invention, these materials can be present as pure components, as a mixture of different components, and in different levels of purity. Therefore, a reference to "additive" is intended to mean, for example, "an additive" or "an additive mixture".

Raw calcium oxide: Raw calcium oxide is a large-scale product and is available in different levels of purity under the name "burnt lime". The method according to the invention is independent of the level of purity. The present method is particularly suitable when the raw calcium oxide is burnt lime obtained from natural limestone by heating at approximately 900-1100° C. Such natural limestone can be calcium-rich limestone, magnesium-rich limestone, or dolomite. Calcium-rich limestone having a low heavy-metal content is preferred. In the context of the present invention, the term "raw" refers to the chemical composition. The term raw calcium oxide therefore includes calcium oxide having a size of 0-130 mm ("lump lime") as well as a size of 0-200 µm ("fine lime").

Additive: The additive results in a surface modification of the milled calcium oxide. Volatile metal compounds (particularly in the case of gas jet mills (M)) or non-aqueous liquids (particularly in the case of wet mills (M)) are suitable for the method according to the invention. The type of modification depends on the selection of the additive and the method conditions, wherein, in principle, the addition can take place via chemical bonding (in particular ionic bonding) or sorption (in particular adsorption).

In one embodiment, the additive is therefore a liquid from the group of $C_{4-20}$ carbonic acids and the derivatives thereof. $C_{4-20}$ carbonic acids, $C_{4-20}$ phosphonic acids, and $C_{4-20}$ sulphonic acids are particularly suitable. Depending on the intended use, certain $C_{4-20}$ carbonic acids, in particular $C_{4-20}$ mono-carbonic acids, are preferred.

According to the invention, such liquids can either (i) consist of these compounds or (ii) contain these compounds and, additionally, a non-aqueous diluting agent. It is advantageous to add a diluting agent in particular when the aforementioned compounds are not present in liquid form under production conditions.

In a further embodiment, the additive is therefore a liquid from the group of $C_{3-20}$ alkyl derivatives of catechol or pyrogallols, such as, for example, gallic acid ester and sorbitol fatty alcohol ether. According to the invention, such liquids can either (i) consist of these compounds or (ii) contain these compounds and, additionally, a non-aqueous diluting agent. It is advantageous to add a diluting agent in particular when the aforementioned compounds are not present in liquid form under production conditions.

In a further embodiment, the additive is a liquid from the group of natural fatty acids, such as stearic acid, palmitic acid, oleic acid, in particular oleic acid and stearic acid. The use of natural fatty acids (or mixtures thereof) is advantageous for various reasons. On the one hand, the product that is obtained is of biological origin, is biologically degradable, and is toxicologically safe. On the other hand, production is unproblematic, since there are neither emissions of VOC nor the risk of explosion. According to the invention, such liquids can either (i) consist of these compounds or (ii) contain these compounds and, additionally, a non-aqueous diluting agent. It is advantageous to add a diluting agent in particular when the aforementioned compounds are not present in liquid form under production conditions.

In a further embodiment, the additive is a liquid from the group of lactic acid derivatives, in particular polylactic acid (PLA). According to the invention, such liquids can either (i) consist of these compounds or (ii) contain these compounds and, additionally, non-aqueous diluting agent. It is advantageous to add a diluting agent in particular when the aforementioned compounds are not present in liquid form under production conditions.

In a further embodiment, the additive is a volatile metal compound from the group of metal halides and metal $C_{1-8}$ alkoxylates. Particularly suitable are $TiCl_4$, $SiCl_4$, $Ti(OEt)_4$, $Ti(OiPr)_4$, $Si(OEt)_4$. The volatile metal halides can be present in a diluting agent, as an option.

Milling aid: A milling aid is intended to mean a component that brings about a reduction in the size of the starting material. Gases (in the case of a milling device M from the group of gas jet mills) or non-aqueous liquids (in the case of a milling device M from the group of wet mills) are suitable for the method according to the invention. It has proven to be important that the water content of the milling aid is low.

A low water content can be ensured by means of correspondingly specified starting materials or by recycling the milling aid. It is assumed that the raw calcium oxide has a dehydrating effect during the milling process.

In one embodiment, the milling aid is therefore an inert gas having a water content of less than 0.1 g water vapor per cubic meter, preferably less than 0.01 g water vapor per cubic meter. This can be ensured by using gases having a corresponding specification. Such gases are commercially available. As an alternative, the gas can be recycled, as described in the following. Preferred gases are nitrogen, noble gases, and dried air.

In a further embodiment, the milling aid is a non-aqueous liquid having a water content of less than 0.1 g water per liter, preferably less than 0.05 g water per liter, at best less than 0.02 g water per liter. This can be ensured by using liquids having a corresponding specification. Such liquids are commercially available. As an alternative, the liquid can be recycled, as described in the following. Preferred liquids are vegetable oils, derivatives of vegetable oils, paraffins, glycols, and glycol ethers.

Depending on the design of the milling device, a solid milling aid (for example, steel or ceramic balls) can be used in addition. This increases the efficiency of step (c), but requires an additional separating step (e).

Step (a): The starting materials are provided in a manner known per se. This can take place in a continuous or discontinuous manner. Expediently, the starting materials are provided from intermediate storage (container (B)), which is preferably shielded with respect to moisture from the surroundings. The raw calcium oxide can be supplied directly from a mill; typically having a particle size of 0-200 μm.

Step (b): For the method according to the invention, it has proven advantageous that the milling process is carried out in the absence of water. Correspondingly, "inertizing" in the context of the present invention is understood to mean the removal of water. This also includes the removal of adsorbed water on surfaces of the milling device. In one embodiment, the inertizing (drying) is carried out by heating the milling device (M) and, optionally, the spraying device (S), optionally under reduced pressure. Heating to 120° C., 1 h, is suitable, for example. This embodiment is particularly suitable for relatively small milling devices and/or discontinuous methods. In an alternative embodiment, the inertizing takes place by means of the raw calcium oxide that is used. In this embodiment, step (c) is carried out until a product having a consistent quality is produced. This embodiment is particularly suitable for relatively large milling devices, in which heating is not possible, and/or in continuous methods. In this embodiment, the method described here is carried out, wherein a product having reduced quality is initially formed, in particular a product having an increased portion of calcium hydroxide and/or an insufficient surface modification. It is assumed that water that is present during the milling process has a disadvantageous effect on the method, but this water is bound by the raw calcium oxide that is used. In this embodiment, the initially produced product is discarded or used in another manner.

In a further alternative embodiment, the inertization is carried out by the raw calcium oxide that is used, with process-internal recycling. In this embodiment, step (c) is carried out until a product having a consistent quality is produced, and the initially produced, low-quality product is used to provide raw calcium oxide (recycling). It is therefore possible to feed this initially produced product to a lime kiln—optionally after further processing steps—in order to obtain raw calcium oxide. In an alternative embodiment, the partially hydrated calcium oxide is utilized externally (for example, in soil stabilization).

Step (c): Basically, all milling devices (milling (M)) that have heretofore been used to mill calcium oxide are suitable for milling. Gas jet milling (jet mill) and wet milling (wet mill) are suitable, in particular. The selection and design of such devices are routine measures to a person skilled in the art.

The milling device must be sealed with respect to the surroundings in order to ensure that the milling takes place in the absence of water. It is thereby ensured that no water (in particular via atmospheric moisture) enters the process. A corresponding seal can be ensured by means of the design of the mill and is a routine measure to a person skilled in the art. Furthermore, it can be advantageous to carry out this step under slight overpressure, for example, 0.1 bar.

In one embodiment, the starting materials calcium oxide, additive, and milling aid are fed to the mill simultaneously. The comminution and the surface modification therefore take place simultaneously.

In a further embodiment, the starting materials calcium oxide and milling aid are fed to the mill simultaneously, and the additive is fed in a downstream spraying device (S). The comminution and the surface modification therefore take place in sequential substeps.

In a further embodiment, the starting materials calcium oxide, additive, and milling aid are fed to the mill simultaneously, and additive is additionally applied in a downstream spraying device (S). Therefore, the comminution and the surface modification take place simultaneously as well as consecutively. This embodiment easily makes it possible to obtain a surface modification with various additives.

Step (d): Known devices (such as sprayers, nebulizers, rotary-drum washers, and the like), which are suitable for coating particles, as is known, are basically suitable for contacting the ground calcium oxide with additive(s). Continuous mixing systems (such as the Vrieco-Nauta Continuous Mixer; for example, Hosokawa Micron LTD) equipped with atomizing nozzles (for the superfine distribution of the additives, for example, from the company Lechler) are suitable, in particular. The selection and design of such devices are routine measures to a person skilled in the art.

In one embodiment, the additive is initially diluted with a diluent and is then contacted with the ground calcium oxide. The diluting agent can be subsequently separated from the product that is obtained. Suitable diluting agents are, for example, anhydrous alcohols (such as ethanol), anhydrous, short-chained hydrocarbons (such as paraffin oil) and anhydrous halogen hydrocarbons (such as methylene chloride). This embodiment is particularly advantageous for the smaller production scale, such as research and laboratory systems.

Step (e): The product obtained from steps (c) and (d) is initially a mixture containing surface-modified calcium oxide, milling aid, and, optionally, additive. In one embodiment, this can be separated in a separating device (T) in a subsequent step. Suitable separating methods and devices are known per se. If the milling aid is a liquid, all devices for separating liquid-solid mixtures, for example, centrifuges and filters, are suitable. If the milling aid is a gas, all devices for separating gas-solid mixtures, for example, centrifugal separators, are suitable.

As mentioned, step (e) is optional; a separate separating step is not absolutely necessary. In the case of gaseous milling aids, these can easily escape into the surroundings at the end of the milling process (c) or spraying process (d).

This is advantageous, in particular, when the milling aid is not recycled. Furthermore, separation can be unnecessary if the milling aid is a suspension, which is intended to be used in the further product application. In this case, in a further embodiment, the invention relates to a method for producing a suspension containing a non-aqueous liquid (continuous phase) and surface-modified calcium oxide particles (disperse phase).

Step (f): If the milling aid and/or additives were separated from the product in step (e), these can be recycled into the method. Optionally, it is advantageous to provide cooling by means of heat exchangers (W) in the recycling.

General method features: A few general and preferred embodiments of the method according to the invention are presented in the following.

The method described here can be designed to be continuous, partially continuous, or discontinuous. In a continuous method, at least the supply to and withdrawal from the milling device (M) are continuous. In a discontinuous method, the supply to and withdrawal from the milling device (M) takes place in a batch-by-batch manner.

The particle size of the surface-modified calcium oxide particles produced according to the invention can cover a wide range and is substantially dependent on the milling device. Typical values for a mean diameter are less than 30 µm, preferably less than 10 µm, particularly preferably less than 2 µm. The particle size can be adapted to the desired application.

The content of additive in the surface-modified calcium oxide particles produced according to the invention can cover a wide range and depends on the quantity used, the particle size, and the method parameters. Typical values are less than 20% by mass, preferably less than 8% by mass, particularly preferably less than 2% by mass, relative to the mass of calcium oxide.

The particle size of the raw calcium oxide that is used can cover a wide range and is substantially dependent on the milling device. Typical values for a mean diameter are particles having a size of 40 micrometers to 2 millimeters. Furthermore, it has proven favorable to reduce the particle size in the milling device by the factor 10 and, preferably, by the factor 20.

The reactivity of the raw calcium oxide that is used can cover a wide range and is substantially determined by the production thereof. The reactivity of calcium oxide is determined according to EN 459-2 (Building Lime—Part 2: Test Methods; Wet Slaking Curve). In this case, the $t_{60}$ value has become accepted as a measurable property of calcium oxide. For the present method, $t_{60}$ values of less than 5 minutes are suitable; less than 2 minutes are preferred; and $t_{60}$ values of 15-60 s are particularly suitable.

As mentioned, the various features of the method according to the invention can be combined with one another in any manner. Certain combinations of features have proven to be advantageous, however; these are particularly preferred and are summarized in the following table:

| Embodiment | A | B | C | D |
|---|---|---|---|---|
| Method | I | I | II | II |
| Milling aid | gaseous | gaseous | liquid | liquid |
| Additive | volatile metal compound | volatile metal compound | carbonic acid derivative | phosphonic acids |
| Type of milling device | jet mill | jet mill | wet mill | wet mill |
| Type of spraying device | 2-phase nozzle | nozzle | nozzle | none |
| Type of separating device | none | cyclone | centrifuge | hydrocyclone |
| Recycle the milling aid? | no | yes | yes | yes |

In a second aspect, the invention relates to surface-modified calcium oxide particles that can be or are obtained according to a method as described above. This aspect of the invention is explained in greater detail in the following.

According to the method described here, it is possible to obtain both already-known and novel surface-modified calcium oxide particles. These novel materials are also the subject matter of the present invention. The invention therefore relates to surface-modified calcium oxide particles that can be obtained according to a method as described herein and to surface-modified calcium oxide particles that are obtained according to a method described herein.

In an advantageous embodiment, the invention relates to surface-modified calcium oxide particles having:
  a particle size of 1 to 10 micrometers;
  a content of oleic acid of 0.5-5%, preferably 0.5-4%; and
  a content of calcium oxide of 95 to 99%.

In an advantageous embodiment, the invention relates to surface-modified calcium oxide particles having:
  a particle size of 1 to 10 micrometers;
  a content of stearic acid of 0.5 to 5%;
  a content of calcium oxide of 95 to 99.5%.

In an advantageous embodiment, the invention relates to surface-modified calcium oxide particles having:
  a particle size of 1 to 10 micrometers,
  a content of dodecylphosphonic acid of 0.25 to 2%;
  a content of calcium oxide of 96 to 99%.

In an advantageous embodiment, the invention relates to surface-modified calcium oxide particles having:
  a particle size of 0.5 to 2 micrometers;
  a content of titanium oxide of 5 to 20%, which is preferably localized on the particle surface; and
  a content of calcium oxide of 80 to 95%.

In an advantageous embodiment, the invention relates to surface-modified calcium oxide particles having:
  a particle size of 0.5 to 2 micrometers;
  a content of silicon oxide of 5 to 20%, which is preferably localized on the particle surface; and
  a content of calcium oxide of 80 to 95%.

In a further embodiment, the invention relates to a mixture of calcium oxide and liquid milling aid. In this embodiment, the primarily created product is not separated. Such a product mixture can be used as a dispersion of surface-modified calcium oxide. In this embodiment, the invention relates to a dispersion, wherein:
  the disperse phase is formed by calcium oxide having a particle size of 0.5 to 2 micrometers, a content of oleic acid or stearic acid of 0.2 to 5%, a content of calcium oxide in the particles of 90 to 99%;
  the continuous phase contains rapeseed oil or is composed thereof; and
  the dispersion has a content of particles of 5 to 20%.

In a third aspect, the invention relates to the use of the calcium oxide particles described herein, and to products that are suitable for these applications. This aspect of the invention is explained in greater detail in the following.

The calcium oxide particles that can be or are obtained according to the method described herein can be used in the heretofore known applications for calcium oxide. The calcium oxide according to the invention, due to the improved properties thereof, exhibits advantages over conventional calcium oxide in these applications. For example, the reduced reactivity toward ambient air results in improved handling and storability.

In addition, further applications result for the calcium oxide particles described here. For example, the calcium oxide particles according to the invention are observed to have improved wettability and/or miscibility, which makes new fields of application possible. The invention therefore also relates to the use of surface-modified calcium oxide particles:
- as plant treatment means;
- as filler, in particular as a functional filler, in plastics;
- as filler (and, optionally, pigment) in varnishes or paints;
- as a food additive;
- as an additive in cosmetics;
- as an auxiliary agent in pharmaceutical products;
- as an additive in paper products;
- as an adhesion promoter in adhesive and polymer formulations; and
- as an auxiliary agent in cement or concrete mixtures.

The calcium oxide particles described herein can be admixed with commercially available products in order to be used in the aforementioned applications.

In one embodiment, the invention therefore relates to a plant treatment means, in particular from the group of fungicides and bactericides, containing calcium oxide particles as described herein. A preferred field of application of the CaO according to the invention is as a locally acting means against plant diseases, in particular false mildew, apple scab, and/or fire blight. Therein, the calcium oxide particles can be present in a wide concentration range, typically in a quantity of 1 to 20% (in particular in the case of liquid formulations) or in a quantity of 75-100% (in particular in the case of solid formulations).

In these cases, the modified CaO described here has a number of advantages: First, the product exhibits a high level of environmental compatibility and is not a water hazard, since CaO has a limited lifetime in the environment, and reacts within hours to days to form limestone (calcium carbonate), which is to say, transitions into a natural and known product. Furthermore, the base material, CaO, and the coating material (additive) are available at favorable prices, and therefore the product is also advantageous in terms of cost-effectiveness. However, the efficacy thereof, in particular, should be emphasized. In comparison experiments (see the following examples 4.1, 4.2 and 4.3), the inventive, modified CaO as well as non-modified (pure) CaO and polymer-coated CaO were investigated in studies of efficacy against plant pests. The series of experiments in examples 4.1, 4.2, and in 4.3, show that the inventive CaO has improved efficacy against microorganisms. This applies, in four comparative examples, for the portion of infested leaves (entries on the left/in the middle in the tables) and for the severity of the infestation (portion of dead leaves, on the right in the tables).

The present invention therefore also relates to the calcium oxide particles described herein as plant treatment means in fruit and vegetable farming and viniculture. The present invention furthermore relates to formulations for plant protection containing the calcium oxide particles described herein, in particular for the treatment of fruit cultures, vegetable cultures, and/or vinicultures.

In a further embodiment, the invention relates to a plastic containing calcium oxide particles as described herein, in particular from the group of polyolefins, polyethers, polysulfones, polyamides, and polyesters. These can also be halogenated, in particular PVC. The calcium oxide particles can be present therein in a wide concentration range, typically in a quantity of 0.2 to 40%.

In a further embodiment, the invention relates to varnishes or paints containing calcium oxide particles as described herein, in particular from the group comprising polyacrylates, polyesters, and polyurethanes. The calcium oxide particles can be present therein in a wide concentration range, typically in a quantity of 0.2 to 40%.

In a further embodiment, the invention relates to foodstuffs containing calcium oxide particles as described herein, in particular from the group comprising baked goods and confectionery, but also fish, meat, and wine. The calcium oxide particles can be present therein in a wide concentration range, typically in a quantity of 0.05 to 2%.

In a further embodiment, the invention relates to cosmetic articles containing calcium oxide particles as described herein, in particular from the group of skin care products and dental care products. The calcium oxide particles can be present therein in a wide concentration range, typically in a quantity of 0.5 to 20%, in particular 0.5 to 10%.

In a further embodiment, the invention relates to pharmaceutical formulations containing calcium oxide particles as described herein, in particular from the group of solid formulations, for example, tablets, powder, suppositories. The calcium oxide particles can be present therein in a wide concentration range, typically in a quantity of 0.05 to 10%.

In a further embodiment, the invention relates to a paper product containing calcium oxide particles as described herein, in particular paper for inkjet printers. The calcium oxide particles can be present therein in an upper layer (in particular the uppermost or second most layer), which absorbs the ink.

In a further application, the invention relates to an adhesive or polymer formulation containing calcium oxide particles as described herein, in particular for the use of sealing materials, joint seals, building seals, and/or polymer/adhesive applications. These adhesive or polymer formulations are used successfully on wet surfaces, in particular. Such formulations are typically semi liquid or highly viscous; the calcium oxide particles can be suspended therein; suitable quantities are in the range of 0.5 to 40%, in particular 1 to 40%.

In a further embodiment, the invention relates to cementitious mixtures as well as concrete containing calcium oxide particles as described herein. The calcium oxide particles can be present therein in a wide concentration range; a person skilled in the art can determine an effective quantity on the basis of test series. The invention therefore also relates to the use of the calcium oxide particles according to the invention in the cement-producing and cement-processing trade ("cement industry").

The examples cited in the following are intended to provide further explanation of the invention; they are not intended to limit the invention in any way.

EXAMPLE 1

In this example, it is shown that raw burnt lime can be ground without negatively influencing the purity.

Mill 2 g of the starting material (particle size less than 200 µm) with 20 ml rapeseed oil and 10 grams of milling balls (zircon, 0.2 mm diameter) in a mill of the planetary-mill type (Fritsch, Pulverisette 7) for 20 minutes at 1100 revolutions per minute).

Quantitative increase of impurities in the treated raw lime.

| No. | Surface treatment | Process-induced calcium hydroxide (% by mass [b]) | Process-induced calcium carbonate (% by mass [b]) |
|---|---|---|---|
| 1 | none (only wet milling according to the conditions specified herein) | <1% by mass | <1% by mass |
| 2 | Soy lecithins (2.5% by mass [a]) | <1% by mass | <1% by mass |
| 3 | Oleic acid (0.25% by mass [a]) | <1% by mass | <1% by mass |
| 4 | Oleic acid (2.5% by mass [a]) | <1% by mass | <1% by mass |
| 5 | Stearic acid (2.5% by mass [a]) | <1% by mass | <1% by mass |
| 6 | Tetradecyl-phosphonic acid (0.25% by mass [a]) | <1% by mass | <1% by mass |

[a] Surface-treatment means: % by mass relative to the total mass of solids
[b] Impurities introduced by milling (milling (entry 1) or milling and surface modification (entries 2-6)).

The table shows the increase in calcium hydroxide and calcium carbonate by means of the method according to the invention. These values are very low and apply for starting materials of high quality (in each case, 0.5% by mass of calcium hydroxide and calcium carbonate) and low quality (3% by mass of calcium hydroxide and 5% by mass of calcium carbonate).

EXAMPLE 2

In this example, it is shown that raw calcium oxide from a lime mill can be used to obtain particles of various sizes. The particle sizes were indicated as hydrodynamic particle size distribution and were determined by means of a Lumisizer. In addition, 0.2-mm balls are used as a milling aid.

Particle size distribution.

| No. | Milling aid | Time (min) | Additive | d10 (µm) | d50 (µm) | d90 (µm) |
|---|---|---|---|---|---|---|
| 7 | 0.2 mm, Diethylene glycol monobutyl ether | 60 | — | 0.075 | 0.13 | 0.4 |
| 8 | 0.2 mm, Paraffin oil | 60 | — | 1.4 | 2.5 | 3.7 |
| 9 | 0.2 mm, Rapeseed oil | 60 | — | 0.8 | 1.3 | 1.8 |
| 10 | 0.2 mm, ethylene glycol | 20 | — | 0.8 | 1.6 | 2.2 |

EXAMPLE 3

In this example, the surface-modified calcium oxide particles are produced. The table, below, shows the process robustness under various conditions.

| No. | Milling aid | Time (min) | Additive | d10 (µm) | d50 (µm) | d90 (µm) |
|---|---|---|---|---|---|---|
| 11 | 0.1 mm/0.2 Rapeseed oil | 60 | — | 0.9 | 1.5 | 2.5 |
| 12 | 0.7 mm/ Rapeseed oil | 60 | — | 0.9 | 1.5 | 2.2 |
| 13 | 0.7 mm/ Rapeseed oil | 20 | Oleic acid, 2.5% by mass | 1.2 | 2.1 | 3.7 |
| 14 | 0.7 mm/ Rapeseed oil | 40 | Oleic acid, 2.5% by mass | 1.2 | 2.0 | 3.8 |
| 15 | 0.7 mm/ Rapeseed oil | 90 | Oleic acid, 2.5% by mass | 0.9 | 1.6 | 2.3 |
| 16 | 0.3 mm/0.4 Rapeseed oil | 60 | Lecithin, 2.5% by mass | 0.9 | 1.5 | 2.2 |
| 17 | 0.7 mm/ Rapeseed oil | 60 | Stearic acid, 2.5% by mass | 3.0 | 5.6 | 6.9 |
| 18 | 0.7 mm/ Rapeseed oil | 20 | Tetradecyl phosphonic acid, 0.25% by mass | 2.4 | 4.5 | 6.6 |

The results show that the various additives are suitable for the method according to the invention. In this case, oleic acid appears to be particularly advantageous due to the narrow particle size distribution.

EXAMPLE 4 (APPLICATIONS IN PLANT PROTECTION)

The following examples show that the surface-modified calcium oxide particles according to the invention have a broad fungicidal and bactericidal effect and, therefore, can be used advantageously in plant protection. The calcium oxide particles used were obtained according to method (II), as depicted above, and have a mean particle diameter of 1-100 micrometers, preferably 1-20 micrometers.

4.1: Fire Blight

Finely pulverized CaO was coated with stearic acid (5% by weight of stearic acid relative to CaO) and was tested, as dust on apple blossoms, against fire blight. The standardized tests were carried out at an institute certified therefor (bioferm Research GmbH, DE).

Coating CaO with stearic acid: 20 g CaO powder was moistened with 1 g stearic acid as solution in ethanol (20 ml) and mixed to form a homogeneous mass. The ethanol-moistened powder was dried on the rotary evaporator with water and air excluded, and yielded a white powder as coated CaO.

Apple blossoms of the Gala type were placed, with the pedicel, in a 10% saccharose solution and were incubated in a humid chamber.

Inoculation/pathogen: Erwinia amylovora strain 385 (Ea385), as a bacterial suspension of fresh cultures with 10 million cells per milliliter, was sprayed onto the blossoms.

Infested blossoms were treated, 1 hour after inoculation, with the coated CaO as dust (test series) or were subjected to the standard treatment (streptomycin sulfate 0.06% as spray solution; control and benchmark).

Evaluation: The blossoms were investigated after 6 days, and analyzed in terms of the pathogen-typical features of an infection (slime spots). 39% of the blossoms without treatment were infested with fire blight. The reduction of the infestation by means of the corresponding treatment was evaluated, in terms of the efficacy of the treatment.

|  | Efficacy of the treatment [%] | Standard deviation [%] |
| --- | --- | --- |
| Streptomycin sulfate 0.06% | 68 | 14 |
| CaO dust coated with 5% stearic acid | 82 | 7 |

4.2: Apple Scab

Modified CaO was tested for the treatment of apple scab (Venturia inaequalis) at an institute approved therefor (FiBL, CH).

Coated CaO:

Coating with stearic acid: according to example 4.1.

Coating with polylactic acid: 20 g CaO powder was moistened with 1 g polylactic acid as a solution in chloroform (20 ml) and mixed to form a homogeneous mass. The moist powder was dried with a rotary evaporator, with water and air excluded, and yielded a white powder which was coated CaO.

Pathogen: Venturia Inaequalis.

Plants: Apple plants of the Jonagold type were cultivated in pots and grew to a 5-leaf stage.

Inoculation: The dried plants were treated with dust or standard means. Three hours later, the plants were sprayed, on all the leaves, with a suspension of 100 thousand germs per milliliter.

Evaluation: Infested plants were evaluated in terms of percent of infested leaves (visible appearance of the disease symptoms). The commercial product "Kocide Opti (a copper preparation)", either as a 0.1% or 0.01% solution, was used as a control for successful treatment. The severity of the infestation is indicated as the portion (%) of infested, dead leaves.

|  | Infested leaves (%) | Standard deviation (%) | Severity (%) | Standard deviation (%) |
| --- | --- | --- | --- | --- |
| No treatment after inoculation | 55 | 11 | 28 | 8 |
| Standard treatment Kocide Opti 0.1% | 17 | 11 | 1.6 | 2.3 |
| Standard treatment Kocide Opti 0.01% | 43 | 8 | 12 | 4.6 |
| Comparison 1 Untreated CaO powder | 46 | 7 | 19 | 2.6 |
| Comparison 2 Polylactic acid CaO | 52 | 7 | 26 | 3 |
| Stearic acid CaO according to the invention | 26 | 6 | 8.7 | 5 |

4.3: False Mildew

Modified CaO was tested for the treatment of false mildew (Plasmopara viticola) at an institute approved therefor (FiBL, CH).

Coated CaO:

Coating with stearic acid: according to example 4.1.

Coating with polylactic acid: according to example 4.2.

Plants: Grapes of the Chasselas type were cultivated in pots and grew to a 4-leaf stage.

Pathogen: Plasmopara viticola.

Inoculation: Moist plants were treated, with dust or standard means. This simulates preventive treatment of the cultures in the event of humid weather conditions, which are feared in terms of mildew propagation. Three hours later, the plants were sprayed, on all the leaves, with a suspension of 50 thousand spores per milliliter.

Evaluation: Infested plants were evaluated as percent of infested leaves (visible appearance of the disease symptoms). A commercial copper preparation (Kocide Opti), either as a 0.1% or 0.01% solution, was used as a control for successful treatment. The severity of the infestation was indicated as the portion (in percent) of infested, dead leaves and is indicated in the following table.

|  | Infested leaves (%) | Standard deviation (%) | Infested, dead leaves (severity) | Standard deviation (%) |
| --- | --- | --- | --- | --- |
| No treatment after inoculation | 93 | 12 | 72 | 15 |
| Standard treatment Kocide Opti 0.1% | 7.5 | 12 | 0.3 | 0.5 |
| Standard treatment Kocide Opti 0.01% | 82.5 | 15 | 26 | 10 |
| Comparison 1 Untreated CaO powder | 72 | 17 | 41 | 11 |
| Comparison 2 Polylactic acid CaO | 92 | 13 | 67 | 8 |
| Stearic acid CaO according to the invention | 43 | 40 | 16 | 18 |

In a second part of the trials, the plants were treated with the same CaO materials directly after inoculation with the causative agent of mildew. This reproduces the field conditions that exist in a treatment of cultures during a propagation of the causative agent.

|  | Infested leaves (%) | Standard deviation (%) | Infested, dead leaves (severity) | Standard deviation (%) |
| --- | --- | --- | --- | --- |
| Comparison 1, post Untreated CaO powder | 96 | 9 | 45 | 17 |
| Comparison 2, post Polylactic acid CaO | 93 | 10 | 52 | 9 |
| Stearic acid CaO, post | 57 | 27 | 7.3 | 5.9 |

The invention claimed is:

1. Surface-modified calcium oxide particles that are prepared by the method comprising the steps of:
    (Method I)
        (a) providing raw calcium oxide, an additive, and a milling aid;
        (b) providing and inertizing a milling device, which is sealed with respect to the surroundings; and
        (c) milling the raw calcium oxide in the presence of the milling aid and the additive in said milling device,
    or
    (Method II)
        (a) providing raw calcium oxide, an additive, and a milling aid;
        (b) providing and inertizing a milling device, which is sealed with respect to the surroundings, and a spraying device;

(c) milling the raw calcium oxide in the presence of the milling aid in said milling device; and (d) contacting the milled calcium oxide with the additive in said spraying device, wherein the milling aid (i) is an inert gas having a water content of less than 0.1 g/m$^3$, or (ii) is a non-aqueous liquid having a water content of less than 0.1 g/l; and wherein the additive is a liquid, which contains at least one compound selected from the group consisting of $C_{4-20}$ carbonic acids, $C_{4-20}$ phosphonic acids, $C_{4-20}$ sulfonic acids, gallic acid ester, sorbitol fatty alcohol ether, oleic acid, stearic acid and polylactic acid;

and wherein the surface-modified calcium oxide particles have a mean diameter of 10 microns or less, and wherein the raw calcium oxide has a $t_{60}$ value of less than 2 minutes, as determined by DIN EN 459-2:2010-12, EN 459-2:2010(E).

2. Surface-modified calcium oxide particles according to claim 1, wherein the particles have:
 a mean particle size of 1 to 10 micrometers;
 a content of oleic acid of 0.5 to 5% by mass; and
 a content of calcium oxide of 95 to 99% by mass.

3. Surface-modified calcium oxide particles, according to claim 1, wherein the particles have:
 a mean particle size of 1 to 10 micrometers;
 a content of dodecylphosphonic acid of 0.25 to 2% by mass; and
 a content of calcium oxide of 96 to 99% by mass.

4. Surface-modified calcium oxide particles, according to claim 1, wherein the particles have:
 a mean particle size of 1 to 10 micrometers;
 a content of stearic acid of 0.5 to 5% by mass; and
 a content of calcium oxide of 95 to 99% by mass.

5. A dispersion comprising:
 a disperse phase comprising 5-20% by mass of surface-modified calcium oxide particles, according to claim 1, wherein the particles have:
  a mean particle size of 0.5 to 2 micrometers;
  a content of oleic acid of 0.2 to 5% by mass; and
  a content of calcium oxide in the particles of 90 to 99% by mass; and
 a continuous phase comprising rapeseed oil.

6. A plant treatment composition selected from the group of fungicides and bactericides, the composition comprising calcium oxide particles according to claim 1 in a quantity of 1-20% by mass.

7. A plastic composition comprising:
 a polymer selected from the group consisting of polyolefins, polyethers, polysulfones, polyamides, and polyesters, which, optionally, are partially or fully halogenated; and
 calcium oxide particles according to claim 1 in a quantity of 0.2-40% by mass.

8. A varnish or paint composition comprising:
 a polymer selected from the group consisting of polyacrylates, polyesters, and polyurethanes; and
 calcium oxide particles according to claim 1 in a quantity of 0.2-40% by mass.

9. A foodstuff comprising calcium oxide particles according to claim 1 in a quantity of 0.05-2% by mass; and
 wherein the foodstuff is selected from the group consisting of baked goods and confectionery, meat and fish products, and alcoholic beverages.

10. A cosmetic article comprising calcium oxide particles according to claim 1 in a quantity of 0.5-20% by mass;
 wherein the cosmetic article is selected from the group of skin care products and dental care products.

11. A pharmaceutical formulation comprising calcium oxide particles according to claim 1 in a quantity of 0.05 to 10% by mass;
 wherein the pharmaceutical formulation is a solid formulation.

12. A paper product comprising multiple layers, wherein an outermost ink-receiving layer comprises surface-modified calcium oxide particles according to claim 1,
 wherein the paper product comprises paper for inkjet printers.

13. An adhesive composition comprising calcium oxide particles according to claim 1 in a quantity of 0.5-40% by mass.

* * * * *